United States Patent
Sperling

(10) Patent No.: US 10,420,643 B2
(45) Date of Patent: Sep. 24, 2019

(54) ROLL-DOWN VASCULAR GRAFT DEVICE

(71) Applicant: CORFIGO, INC., Montclair, NJ (US)

(72) Inventor: Jason Scott Sperling, Upper Saddle River, NJ (US)

(73) Assignee: Corfigo, Inc., Montclair, NJ (US)

( * ) Notice: Subject to any disclaimer, the term of this patent is extended or adjusted under 35 U.S.C. 154(b) by 21 days.

(21) Appl. No.: 15/375,207

(22) Filed: Dec. 12, 2016

(65) Prior Publication Data
US 2017/0086964 A1    Mar. 30, 2017

Related U.S. Application Data

(63) Continuation-in-part of application No. 12/888,986, filed on Sep. 23, 2010, now abandoned.

(60) Provisional application No. 61/245,540, filed on Sep. 24, 2009.

(51) Int. Cl.
*A61F 2/06* (2013.01)
*A61F 2/24* (2006.01)

(52) U.S. Cl.
CPC ...... *A61F 2/2472* (2013.01); *A61F 2250/001* (2013.01); *A61F 2250/0007* (2013.01)

(58) Field of Classification Search
CPC ....................................................... A61F 2/06
See application file for complete search history.

(56) References Cited

U.S. PATENT DOCUMENTS

| 6,524,322 | B1 | 2/2003 | Berreklouw |
| 2008/0009747 | A1 | 1/2008 | Saadat et al. |

OTHER PUBLICATIONS

Lansac, Emmanuel et al., "An External Open Ring for Isolated Aortic Valve", MultiMedia Manual of Cardiothoracic Surgery, pp. 1-7, published Mar. 2007.
Zehr, Kenton J. et al., "Clinical Introduction of a Novel Prosthesis for Valve-Preserving Aortic Root Reconstruction for Annuloaortic Ectasia", The Journal of Thoracic and Cardiovascular Surgery, pp. 691-699, published in 2000, downloaded from jtcs.ctsnetjournals. org on Jul. 4, 2011.
Ghandour, Mishal et al., "A Simple Method for Intraoperative Visualization of the Repaired Aortic Valve", Journal of Thorac Cardiovascular Surgery, pp. 632-634, published in 1994.

*Primary Examiner* — Matthew W Schall
(74) *Attorney, Agent, or Firm* — Davis, Brown, Koehn, Shors & Roberts, PC; Sean D. Solberg

(57) ABSTRACT

A prosthetic device for attachment to a vascular structure includes a body with an axial length configured to be adjustable by manipulation of at least one design feature but not materially affected by simple luminal pressurization. The at least one design feature includes at least one of a reducing mechanism or a purse-string provided along at least part of a circumference of the body to actuate reduction of a diameter of the device. The prosthetic device may include a body with an axial length configured to be adjustable and at least one roll-down segment at one end of the body. The at least one roll-down segment may be configured to be facilitated or supported by integrated shape memory materials to maintain the roll-down characteristics.

20 Claims, 14 Drawing Sheets

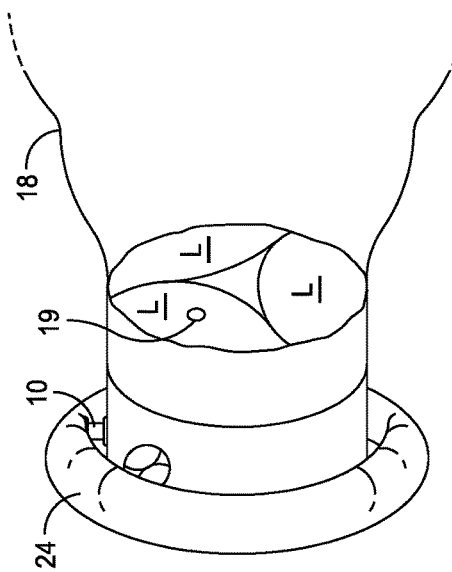
FIG. 8C
FIG. 8F
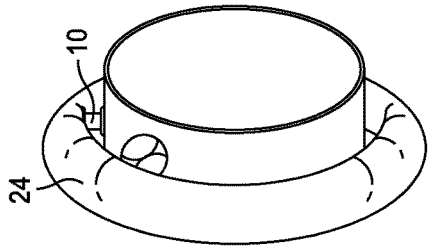
FIG. 8B
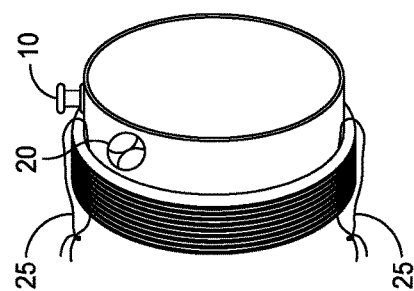
FIG. 8E
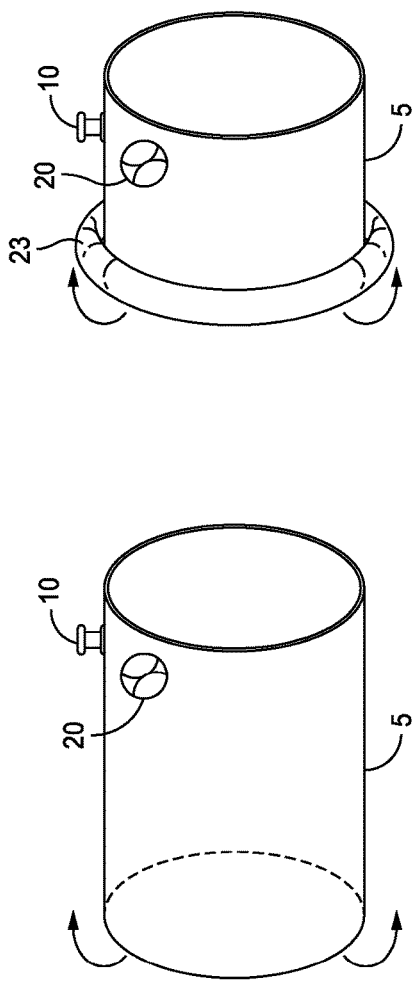
FIG. 8A
FIG. 8D

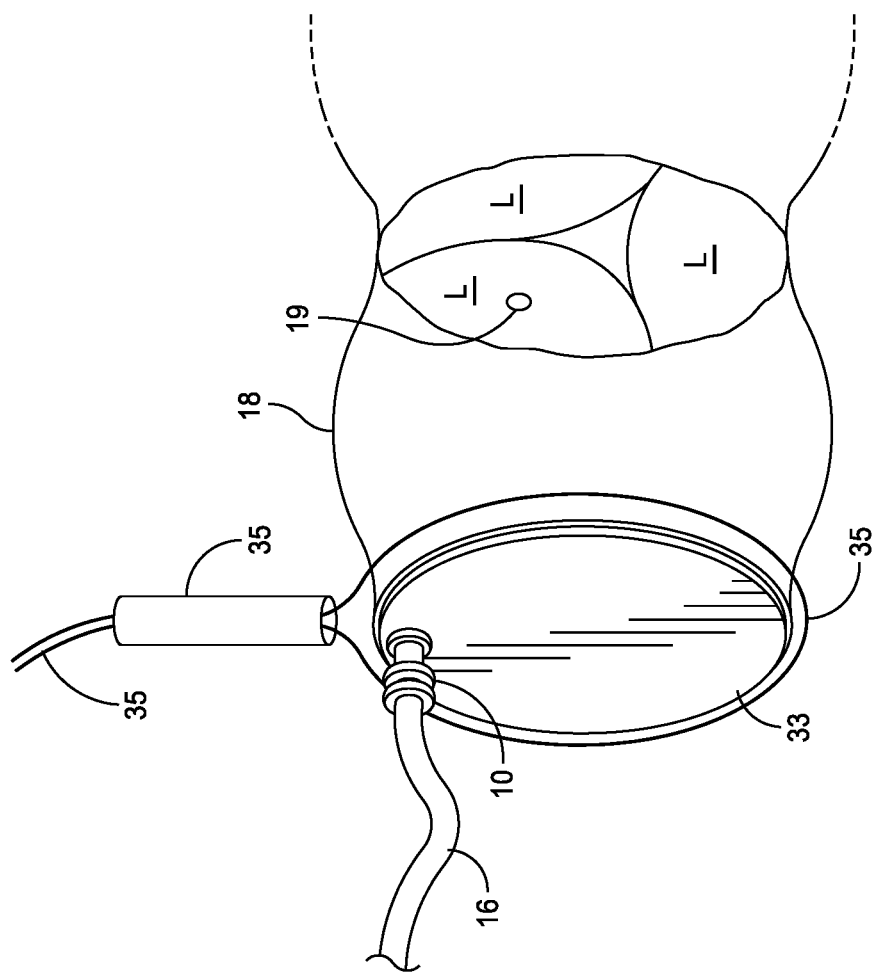

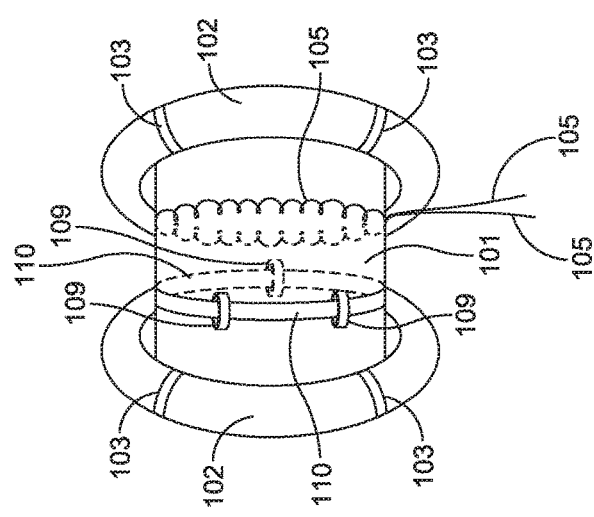
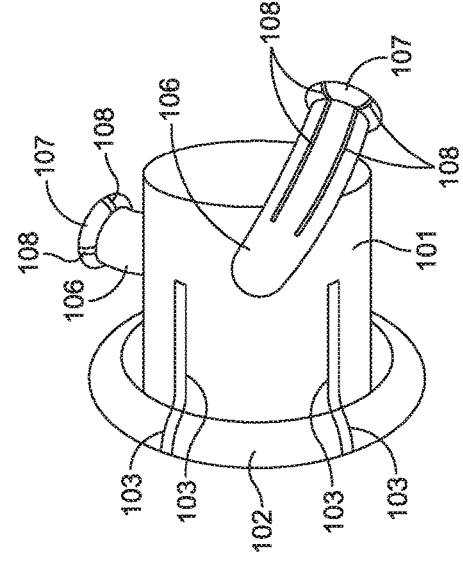

ROLL-DOWN VASCULAR GRAFT DEVICE

RELATED APPLICATION

This application is a continuation-in-part of U.S. application Ser. No. 12/888,986, entitled "APPARATUS FOR SIMULATION OF DIASTOLE AND VISUALIZING THE DIASTOLIC STATE OF AN AORTIC VALVE AND ROOT DURING CARDIAC SURGERY," filed Sep. 23, 2010, which claims priority under 35 U.S.C. § 119(e) to U.S. Provisional Application No. 61/245,540, entitled "APPARATUS FOR SIMULATION OF DIASTOLE AND VISUALIZING THE DIASTOLIC STATE OF AN AORTIC VALVE AND ROOT DURING CARDIAC SURGERY," filed Sep. 24, 2009, both of which are hereby incorporated by reference in their entirety for all purposes.

BACKGROUND OF THE DISCLOSURE

1. Field of the Disclosure

This disclosure relates generally to methods and devices for performing vascular and aortic surgery, and more particularly, to methods and devices for prosthetic replacement, bypass or access grafts that can be more ideally size-matched for both length and caliber to avoid unwanted native vessel and prosthetic graft distortion and related malfunction or complications.

2. Discussion of Related Art

Vascular obstructive and aneurysmal diseases are leading causes of morbidity and mortality in the United States and abroad. During surgery to replace, bypass or access diseased or dysfunctional blood vessels or vascular structures, the use of a prosthetic graft is often required. Most of the time, when one blood vessel is connected to another (or to another prosthetic vascular graft), a distance between the two vessels is merely estimated, often incorrectly. Over-estimation of a needed prosthetic graft length can lead to kinking and obstruction of the graft due to redundancy, which can lead to either early or late procedural complications. Under-estimation of prosthetic graft length can lead to tension on the vascular connections, leading to bleeding, distortion of recipient vessels, and late complications, such as pseudoaneurysms. Another miscalculation of needs can relate to over-estimation of prosthetic graft diameter. If the selected prosthetic graft diameter exceeds that of the recipient vessel in the setting of an intended "end-to-end" graft to vessel vascular connection, a size mismatch often leads to bleeding at the site of vascular connection. In addition, most vascular procedures will require at least two separate vascular connections, and these connections are generally visually hindered by the presence of longer segments of prosthetic graft material. The vascular connection becomes technically much easier with shorter (and shortest) graft lengths, due to better visualization and manipulation of the interaction of the prosthetic graft with the recipient vessel.

A prosthetic vascular graft has been conceived to overcome the aforementioned limitations of standard vascular prosthetic devices. Current devices are typically constructed of knitted or woven Dacron or polyester material, or of another material, such as polytetrafluoroethylene (PTFE). These devices are typically of a uniform caliber and length, and some newer devices can taper by increasing or decreasing to a different caliber, in a predetermined and non-adjustable fashion. Other common existing devices appear corrugated, and can be stretched from a static baseline length to a longer length by traction, or more commonly, graft length is increased in a somewhat less predictable fashion after it become pressurized with flowing blood after completion of the vascular connections. It is in precisely in these situations when incorrect estimation of "final" (pressurized) graft length becomes apparent, with grafts that are too long becoming kinked due to redundancy and grafts that have been purposely trimmed to be shorter (to avoid redundancy and kinking) turn out to be too short, with graft/vascular connections that are ultimately under tension in their final configuration.

SUMMARY OF THE DISCLOSURE

Different embodiments of the device allow for reversible, water-tight attachment of a chamber or disc to either the opened/transected aorta itself, or to a short open tube, typically of a prosthetic material i.e., fabric, polyester or other material than is sutured to a portion of the opened or transected aorta or aortic root. In some versions of this device, methods for reversible attachment may also be engineered into the short open tube. In other iterations, a device is sutured directly to the opened or transected aorta, and can expand to enable valve assessment and then contract down to a position very close to the suture line, in order to re-access the valve for re-repair, etc. A method is described for surgery to correct aortic valve leaking, wherein the surgeon manipulates aspects of the ventriculo-aortic junction, the area above the aortic valve, and the aortic valve leaflets themselves and assesses the valve repair using said chamber or disc to assess the valve repair over and over again until the aortic valve is rendered competent.

In one embodiment, a device that comprises a partially or completely transparent chamber is attached to the opened or transected aorta at the site of the incision made to access and visualize the aortic valve during open heart surgery. If aortic root (aneurysm) replacement is required, or a complete transection of the aorta is desired to access the valve, the chamber attaches to a short open tube of fabric or other material, which is sutured to the aorta or ventriculo-aortic junction. The device will be available in size ranges corresponding to typical sizes of the anatomic sino-tubular junction, roughly 20 to 40 mm. The chamber proximal end is configured to have a reversible attachment mechanism (e.g., magnetic, external cinching or snaring over a groove or ridge, vacuum or other mechanism). A feature of the device is a mechanism for viewing the aortic valve through at least a portion that is transparent, or by incorporating a mechanism for videoscopic or ultrasonic assessment of an aortic valve. Yet another feature is the ability to simulate the diastolic phase of the cardiac cycle relative to the aortic root by creating closed space pressurization of the device attached to the surgically transected aorta or short open tube, and filling of the chamber with fluid in a generally water-tight fashion, and monitoring of the closed system with pressure sensors and relief valves to reproduce the normal physiologic characteristics of diastole. The distal end of the chamber may be closed, or tapered to a smaller open end to connect to tubing that will deliver fluid into the chamber, with approximate sizes ranging from ³⁄₁₆ inch to ½ inch diameter. There may be Luer lock connector or other port attachment sites for pressure monitoring or relief valves, or delivery of said fluid. The ports may comprise one-way valves or entry sites for introduction of video-scopes or ultrasound transducers into the chamber. The device is then removed in order to gain the most direct access to the aortic valve and root for repair or re-repair the valve until a satisfactory result is obtained.

Various iterations of the device are conceived where some of the viewing area comprises a magnification or distortion lens, as well as wherein the attachment mechanism is aided by incorporation of silicone washers, for example. Where magnets are used in either or both of the chamber proximal end and the short open tube, there may be tabs associated with each to ease un-coupling. In another embodiment, the device is comprised of a transparent disc, rather than a chamber, reversibly attachable to the aorta or to a short open tube in a water-tight fashion, as described. A reversible attachment mechanism may have a peripheral groove or ridge on the proximal end of the chamber or disc so that a snare or tourniquet can be secured externally around the aorta or short open tube, to effect a water-tight seal.

Other embodiments of the device may include attaching an expandable tube or cylinder to the transected aorta to the function as the "chamber" described above. Valve assessment may be accomplished by closed pressurization of the expandable tube with fluid or blood. The expandable tube may incorporate a transparent window or have ports for indirect visualization of the valve with, for example, videoscopy or ultrasound. The distal end of the tube can be clamped with a standard vascular clamp in order to close the system for valve assessment. A feature of this embodiment is that after a valve assessment is done, the tube or cylinder is collapsed down to a small length, e.g., less than 50% of its expanded length but ideally down to less than 20 mm so that access to the valve will be unimpeded for repair or re-repair. These collapsible designs may do so by, for example, roll-down or fold-down (accordion-type) mechanisms. This design eliminates the need to physically attach a chamber to the short tube or aorta over and over again. A similar iteration would be where the tube was not collapsible, but still comprised a transparent window or ports for ultrasound/video. The valve can be re-accessed over and over again by making an incision in the tube and suturing it together to create a closed system for valve assessments.

Either the expandable tube/cylinder or the short open tube may include a cinching mechanism, possibly by pre-sutured purse-string or strings circumferentially woven into it. The purse-strings may also pass through other material to buttress the needle entry sites. This construction is intended to manipulate the size of the aorta above the valve or at the level of the aortic root (which may be mechanisms used to restore leaking valve competency), as well as to provide a mechanism for securing a transparent disc or chamber that has a peripheral groove or ridge to mate with the cinching mechanism.

The method in which the device will be utilized is as follows. Open heart surgery is performed in the standard fashion, using the heart-lung machine. The aorta is opened above the sino-tubular junction, and a dissection is made down to the ventriculo-aortic junction if aortic root replacement or manipulation is required. If a modular device is used, a short open tube is sewn either to the aorta above the valve or to the ventriculo-aortic junction (i.e., during aortic root replacement with aortic valve re-implantation). A closed system is created by attaching a transparent chamber or disc to either the short open tube, or to the opened (transected) aorta itself. Clear fluid (or blood, if ultrasound is used), such as crystalloid cardioplegia (a standard solution used to maintain and protect an arrested heart), is pumped through plastic tubing connected to the chamber or disc which is filled with the fluid while monitoring flow amount and pressure in the aortic root, in a generally water-tight fashion. The surgeon directly (through the transparent chamber) or indirectly (by video or ultrasound) visualizes the aortic valve in a physiologic closed position, and any mechanism of retrograde leaking is identified. Fluid flow is stopped, and the chamber/disc is detached in order to have the most direct access possible to the aortic valve. The valve is repaired or re-repaired as needed, and the device is then re-attached for a new assessment, and repeated until a satisfactory result is obtained (minimal residual leaking). The device is removed for the last time, and the aortic incision is re-approximated. The patient is separated from the heart-lung machine and clinical assessments are made as usual.

In one embodiment, the clinical problem being addressed is the difficulty in repairing leaking aortic valves because the etiology of valve leaking cannot be easily elucidated with conventional means, and because repair maneuvers cannot be adequately tested until after the patient is weaned off of the heart-lung machine, which is inconvenient. The proposed methods and devices may be used to reversibly create a generally water-tight closed space in the aortic root: the space between the ventriculo-aortic junction (where the aortic valve emerges from the left ventricle) and the tubular ascending aorta (above the aortic valve) after an incision is made in the aorta above the valve. A device that is usually at least partially transparent is secured into position above the valve, and the aortic root is pressurized with fluid, and the aortic valve is visualized. These devices are especially intended to allow the surgeon to visualize the aortic valve in its closed position, under conditions that are physiologic (fluid infusion into the aortic root, with pressures up to 150+ mmHg), and to identify how retrograde leaking is occurring. There are two general ways in which these devices would be used. The first, is where an incision is made just above the aortic valve and a device can be secured within the opened aorta in a reversible fashion (e.g., cinching or snaring). The causes of the leak are determined, and the device is removed and the aortic valve repaired. The device is then re-attached/secured in position and the aortic root is again pressurized with fluid to see if the repair was successful. If not, the cause is seen and the device removed so that re-repair can be attempted. This cycle continues until a satisfactory result is obtained, and the aorta is closed to complete surgery. The second general way in which this device can be used is to have it couple with a short open tube, usually of fabric, and this short open tube will have complementary features to enable reversible attachment of the device described above, with more versatility as to how reversible attachment can be achieved. The short open tubes would generally be of identical material and characteristics of commercially available fabric vascular grafts, and with removal of any associated connecting mechanism located at an end of the tube, it would be able to be appropriately used as a vascular replacement graft if desired. This is particularly anticipated for aortic root aneurysm surgery where aortic valve re-implantation is planned: where the aortic valve is dissected free from its native attachments and re-implanted into a vascular fabric graft. One additional feature is the ability to manipulate the diameter of the short open tubes, possibly by integrated purse-string or strings, which may be desirable during some forms of aortic valve repair. In some iterations, the short open tube itself may be discontinuous (e.g., a cut circle in axial view) so that it can be slid under the still-intact (only partially transected) aorta during aortic valve repair.

One aspect of the disclosure is directed to a device for evaluating an aortic valve after opening an aorta distal to the aortic valve. In one embodiment, the device comprises a body defining a chamber. The body has a generally circular proximal open end and a distal end, the proximal open end being configured to be reversibly attachable to one of the aorta and a short open tube distal to the aortic valve in a generally water-tight fashion. At least a portion of the body is transparent to view the aortic valve.

Embodiments of the device may include configuring the body in a generally cylindrical in shape in which the proximal open end of the body has a diameter of 20 to 40 mm and the distal end tapers from the proximal open end to define an opening with a diameter of less than 15 mm. The portion of the body may further include at least one magnifying or distortion lens. The proximal open end may be configured to be reversibly attachable to the short open tube that is fabricated from flexible material, an end of the short open tube having an opening with a diameter of 20 to 40 mm. The short open tube may embody a sewing cuff having an integrated purse-string or snare. The device may further comprise a mechanism for reversible attachment of the body to the short open tube. In one embodiment, the mechanism includes at least one magnet associated with either or both of the short open tube and the proximal open end of the body. At least one of the proximal open end of the body and short open tube may comprise a water-tight washer of silicone or other material. The device may further comprise a mechanism for reversible attachment, the mechanism including at least one generally circumferential groove or ridge at or near the proximal open end of the body such that an external snare or purse-string is used to secure the at least one groove or ridge within the aorta or short open tube. In one embodiment, the mechanism for reversible attachment may comprise at least two sets of joining clasps on both the body proximal open end and the sewing ring. The body may further include at least one port.

Another aspect of the disclosure is directed to a device for evaluating an aortic valve after opening an aorta distal to the aortic valve, the device comprising a generally circular disc having a transparent portion to view the aortic valve, the disc being configured to be reversibly attachable to one of the aorta or a short open tube distal to the aortic valve in a generally water-tight fashion.

Embodiments of the device may include configuring the disc to have a diameter of 20-40 mm. The disc may further comprise at least one magnifying or distortion lens. The disc may be configured to be reversibly attachable to the short open tube that is fabricated from polyester or other fabric material having diameter of 20-40 mm or to the aorta itself. The short open tube may comprise at least one integrated purse-string or snare. The at least one of the disc and the short open tube may include a water-tight washer. The device may further comprise a mechanism for reversible attachment of the disc to the aorta distal to the aortic valve, the mechanism including at least one magnet provided in one of the disc and the short open tube. In one embodiment, a mechanism for reversible attachment of the disc to the aorta distal to the aortic valve includes at least two sets of joining clasps on both the disc and the short open tube. The device may further comprise a mechanism for reversible attachment of the disc to the aorta or the short open tube distal to the aortic valve, the mechanism including at least one generally circumferential groove or ridge around the disc such that an external snare or purse-string is used to secure the at least one groove or ridge within the aorta or the short open tube. The disc may further comprise at least one opening or port.

Yet a further aspect of the disclosure is directed to a device for evaluating an aortic valve after opening an aorta distal to the aortic valve, the device comprising a non-rigid cylinder having a 20-40 mm diameter proximal end, wherein at least a portion of the cylinder being transparent to view the aortic valve. In one embodiment, the tube or cylinder is collapsible to a length of less than 50% of its extended length, by one of a roll-down or a folding mechanism.

Another aspect of the disclosure is directed to a prosthetic device for attachment to a vascular structure. In one embodiment, the device comprises a body with an axial length configured to be adjustable by manipulation of at least one design feature but not materially affected by simple luminal pressurization.

Embodiments of the device further may include the at least one design feature having at least one of a reducing mechanism or a purse-string provided along at least part of a circumference of the body to actuate reduction of a diameter of the device.

A further aspect of the disclosure is directed to a prosthetic device comprising a body with an axial length configured to be adjustable and at least one roll-down segment at one end of the body.

Embodiments of the device further may include the at least one roll-down segment being configured to be lengthened by unrolling or re-shortened to an original length by re-rolling. The at least one roll-down segment may include one roll-down segment positioned at one end of the body and another roll-down segment positioned at an opposite end of the body. The body may include side branch prosthetic grafts that each include a roll-down segment configured to be lengthened. The at least one roll-down segment may be configured to be facilitated or supported by integrated shape memory materials to maintain the roll-down characteristics. The device further may comprise at least one reducing mechanism or purse-string positioned along at least part of a circumference of the body to actuate reduction of a diameter of the body. The at least one reducing mechanism or purse-string may include an integrated system of belt loops and belts fabricated from a prosthetic material that can be tightened.

The present disclosure will be more fully understood after a review of the following drawing figures, detailed description and claims.

DESCRIPTION OF THE DRAWINGS

In the drawings, each identical or nearly identical component that is illustrated in various figures is represented by a like numeral. For purposes of clarity, not every component may be labeled in every drawing. For a better understanding of the present disclosure, reference is made to the figures which are incorporated herein by reference and in which:

FIGS. 8A-8F illustrate several mechanisms by which an expandable device may be collapsed to a smaller length in order to make valve repair assessments;

FIG. 11 illustrates another embodiment of a transparent disc that is reversibly attachable to the aorta itself, by external snaring that couples with a groove or ridge on the disc, the disc having a port of entry for delivering fluid into the aortic root;

FIGS. 14A and 14B illustrate other embodiments of the vascular graft device, with roll-down segments at opposing ends, mechanisms for reducing the caliber of the cylinder and also cylindrical graft side branches with their own roll-down components originating from the non-rolled portion of the primary vascular graft.

DETAILED DESCRIPTION OF THE DISCLOSURE

Figure 1:
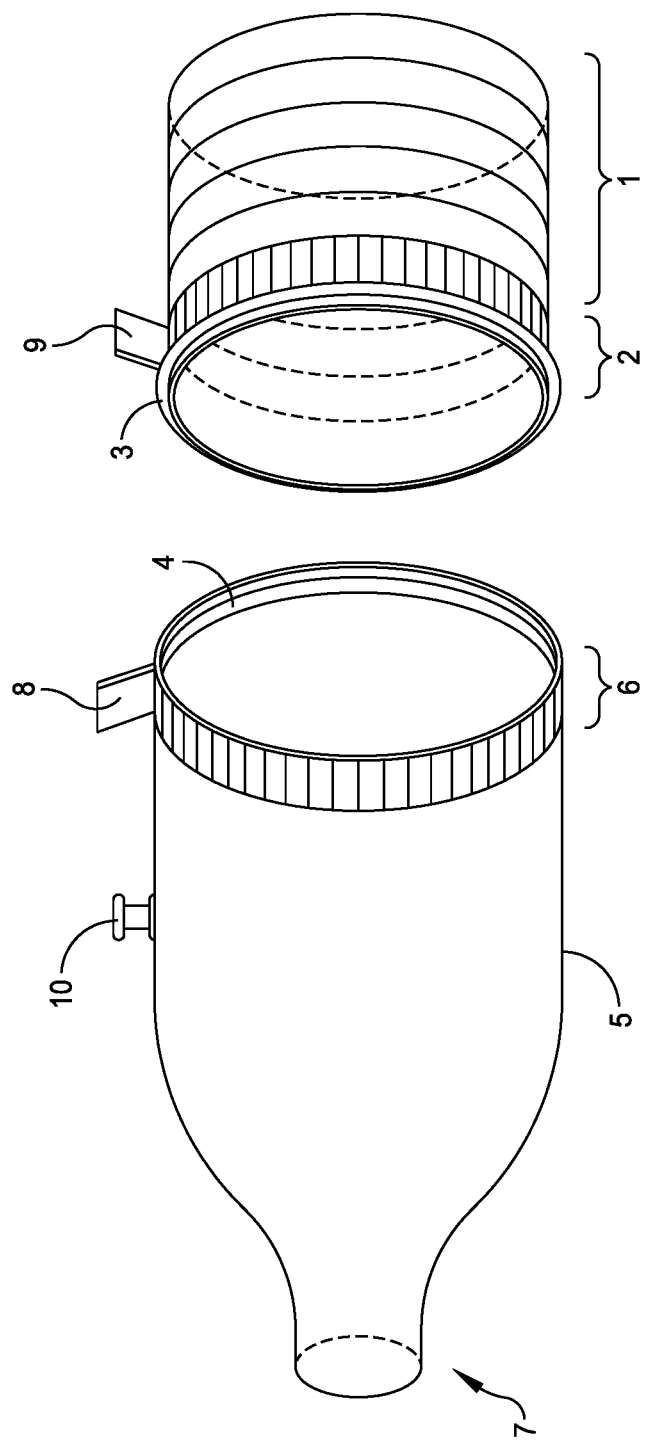
FIG. 1 is an exploded representation of one embodiment of a device showing a short open tube separated from a reversibly attachable chamber.

This disclosure is not limited in its application to the details of construction and the arrangement of components set forth in the following description or illustrated in the drawings. The principles disclosed herein are capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

With reference to FIG. 1, a short open tube 1 may be fabricated from polyester, Dacron, expanded polytetrafluoroethylene, or any other material (e.g., xenograft tissue, such as bovine pericardium or porcine small intestinal submucosa) suitable for suturing to the native aorta (i.e., the large, main blood vessel that exits the heart). The short open tube 1 is generally a short, open-ended cylinder, with diameter ranging 20 to 40 mm, corresponding to the range of size of the normal aorta at a level above the valve (i.e., the sinotubular junction). The short open tube 1 is sewn to the transected aorta after the heart is stopped during open heart surgery. A reversible connecting mechanism 2 of the short open tube 1 and a proximal open end 6 of chamber 5 each comprise open rings and mechanisms for reversibly attaching to one another. Specifically, the reversible connecting mechanism 2 and the proximal open end 6 each exhibit a generally circular shape and whose unattached surfaces may respectively comprise washer rings 3, 4 to effect a generally water-tight seal when adjoined. Both the distal end of short open tube 1, comprising connecting mechanism 2, and the proximal open end 6 of chamber 5 represent open rings and externally have attached fixation tabs 8 and 9 for grasping when attempting to separate the device after it has been assembled. The chamber 5 may be dome shaped, and has a proximal open end 6 and a distal end 7. In this configuration, the distal end 7 tapers to a smaller generally cylindrical opening for attachment to tubing when the device is in use. Chamber 5 may also have one or more Luer lock connectors or port attachments 10 for fixation of additional devices fitted to the Luer lock connector, such as syringes, pressure gauges, tubing, overflow valves, etc.

Figure 2:
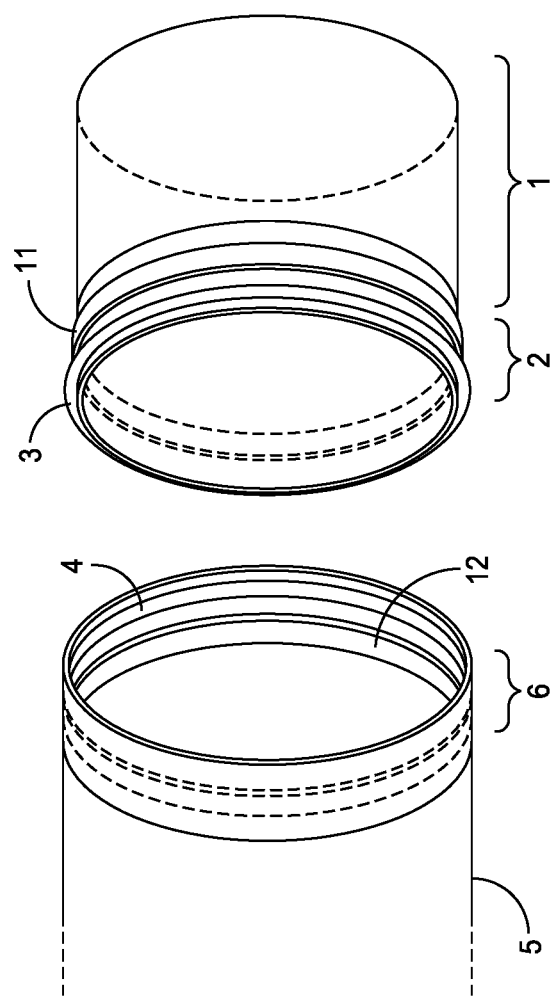
FIG. 2 represents the device showing a mechanism to reversibly attach the chamber to the short open tube, such as by magnetic force.

With reference to FIG. 2, an embodiment of the reversible attachment mechanism is illustrated. The connecting mechanism 2 of the short open tube 1 may be comprised of a silicone or rubber washer 3 on its distal end. In this embodiment of the disclosure, within the center of the connecting mechanism 2 is either a ferro-magnetic core or a magnet 11. Similarly, the proximal open end 6 of chamber 5 may be comprised of a silicone or rubber washer 4, and in this embodiment, within the center of proximal open end 6 is a complimentary magnet or ferro-magnetic core 12 in the shape of a ring. Magnets used may comprise rare-earth magnets. The magnetic forces are sufficient to enable reversible joining of the proximal open end 6 of the chamber 5 to the short open tube 1 by connecting mechanism 2, and resist separation at chamber pressures of up to 350 mm Hg.

Figure 3:
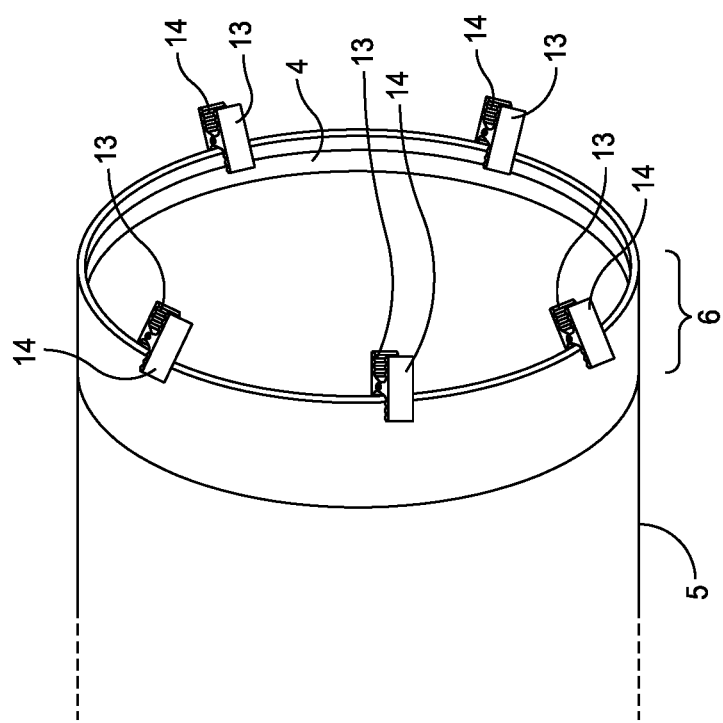
FIG. 3 is an enlarged representation of an embodiment of the disclosure showing an alternate mechanism for reversibly attaching the chamber to the short open tube by clips.

FIG. 3 is yet another embodiment of a method by which the proximal open end 6 of the chamber 5 may be reversibly joined to the short open tube (not shown). Internal and external pinch tabs 13, 14 snap into place over the distal end of the short open tube (not shown). A silicone or rubber washer 4 ensures water-tight seal, and pinch tabs 13, 14 are engineered to resist separation from the short open tube at chamber pressures up to 350 mm Hg.

Figure 4:
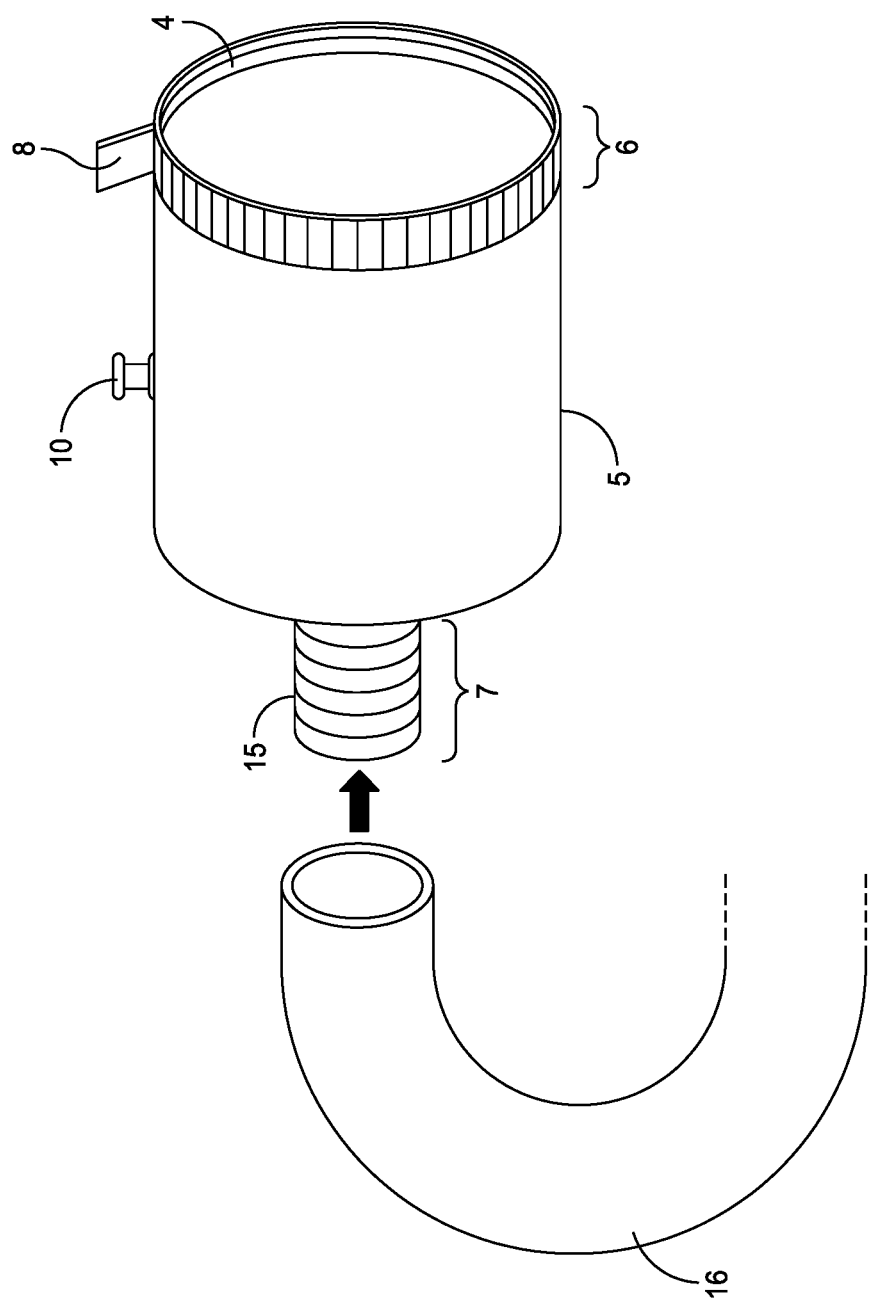
FIG. 4 is a representation of a device comprising a chamber and tubing connected to a distal end of the chamber.

FIG. 4 is a representation of another embodiment of the chamber, which is generally cylindrical shaped. Distal end 7 comprises a short inflow cylinder 15, while the remainder of the distal end is closed. Both inflow tubing 16 and inflow cylinder 15 are of a caliber generally in the ³⁄₁₆ inch to ½ inch range.

Figure 5:
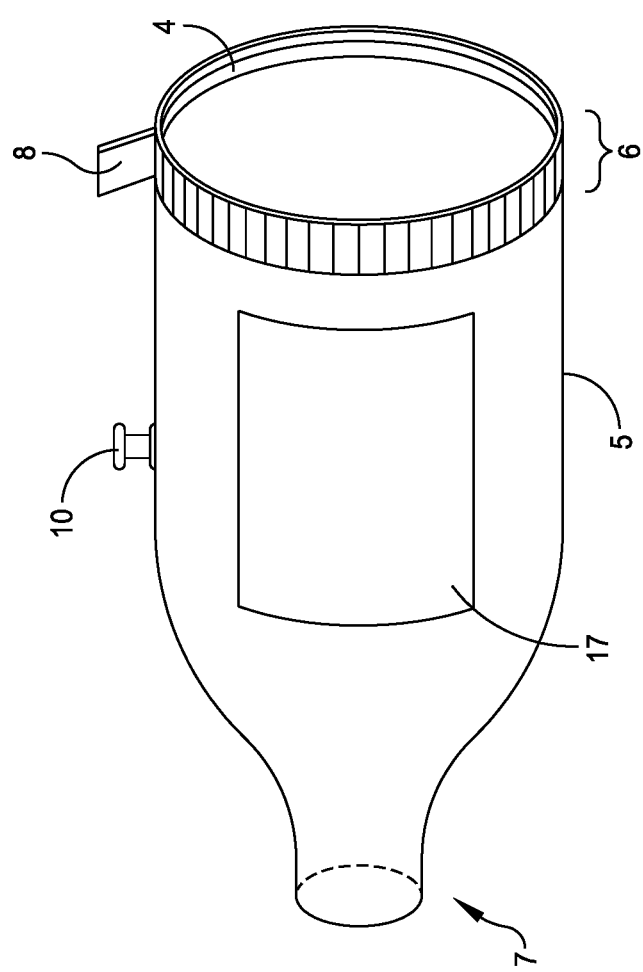
FIG. 5 is another representation of a chamber illustrating a transparent window or magnifying/distortion window of the chamber.

FIG. 5 is yet another representation of chamber or cylinder/tube 5, illustrating a transparent window, or a magnifying or distortion lens 17 within at least one location in the chamber or cylinder/tube. In this illustration, the distal end 7 is tapered to receive tubing in order to fill the chamber and aortic root with fluid in a generally water-tight fashion. Another iteration would have the chamber 5 be a tube or cylinder of fabric or other material that is open on the distal end and can be clamped with a vascular clamp in order to close the system and allow pressurization with fluid by a needle puncture or a Luer lock connector or other ports 10.

Figure 6:
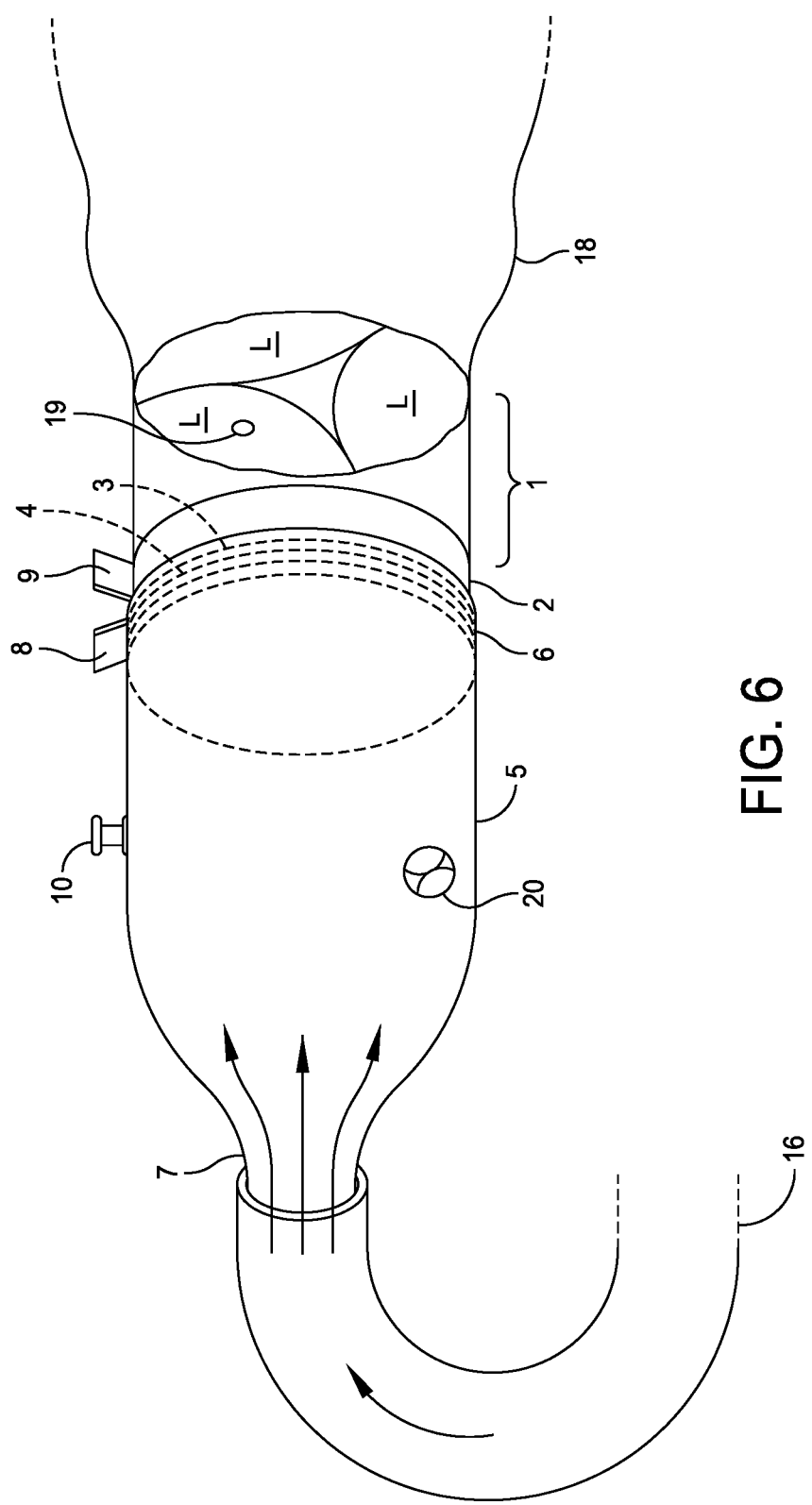
FIG. 6 is another representation of the method and an embodiment of a device having a proximal open end joined to a short open tube, with the aortic valve visualized as fluid fills the chamber and attached aortic root in a generally water-tight fashion.

Aortic valve repair is performed using this method and a configuration of the device, which is shown in FIG. 6. As shown, the proximal open end 6 of chamber 5 is reversibly joined to the short open tube 1 by the connecting mechanism 2, both adjoined by touching silicone or rubber washers 3, 4, by mechanisms inclusive but not limited to the connecting mechanisms previously described. Inflow tubing 16 is joined to the tapered distal end 7 of chamber 5, which may be transparent, contain a transparent window, or have one or more one-way valves or ports 20 for insertion of a videoscope or ultrasound probe, for example. Luer lock connector or port 10 and others not shown are used for removal of air, measuring chamber pressure, overflow valves as the chamber 5 and attached aortic root 18 are filled with clear fluid, i.e., crystalloid cardioplegia (substance used to maintain an arrested heart during surgery) provided by inflow tubing 16. The short open tube 1 may be sutured to the aortic root 18 above the level of the valve, or to the ventriculo-aortic junction, as in aortic root replacement with aortic valve re-implantation. The aortic valve leaflets L and the left main coronary artery 19 are physically located proximal to the junction between the chamber 5 and the short open tube 1 and within the aortic root 18, but can be visualized through the chamber 5 under conditions that simulate diastole (the period of time where the aortic valve is closed). If residual valve leaking is observed, the fixation tabs 8 and 9 may be grasped to facilitate separation of the transparent chamber 5 from the short open tube. Re-repair of the aortic valve is performed, and these steps are repeated until minimal aortic valve leaking is observed within the chamber under simulated diastolic conditions.

Once the repair is deemed to be satisfactory, the short open tube 1 may be transected or removed and the aorta closed.

Figure 7:
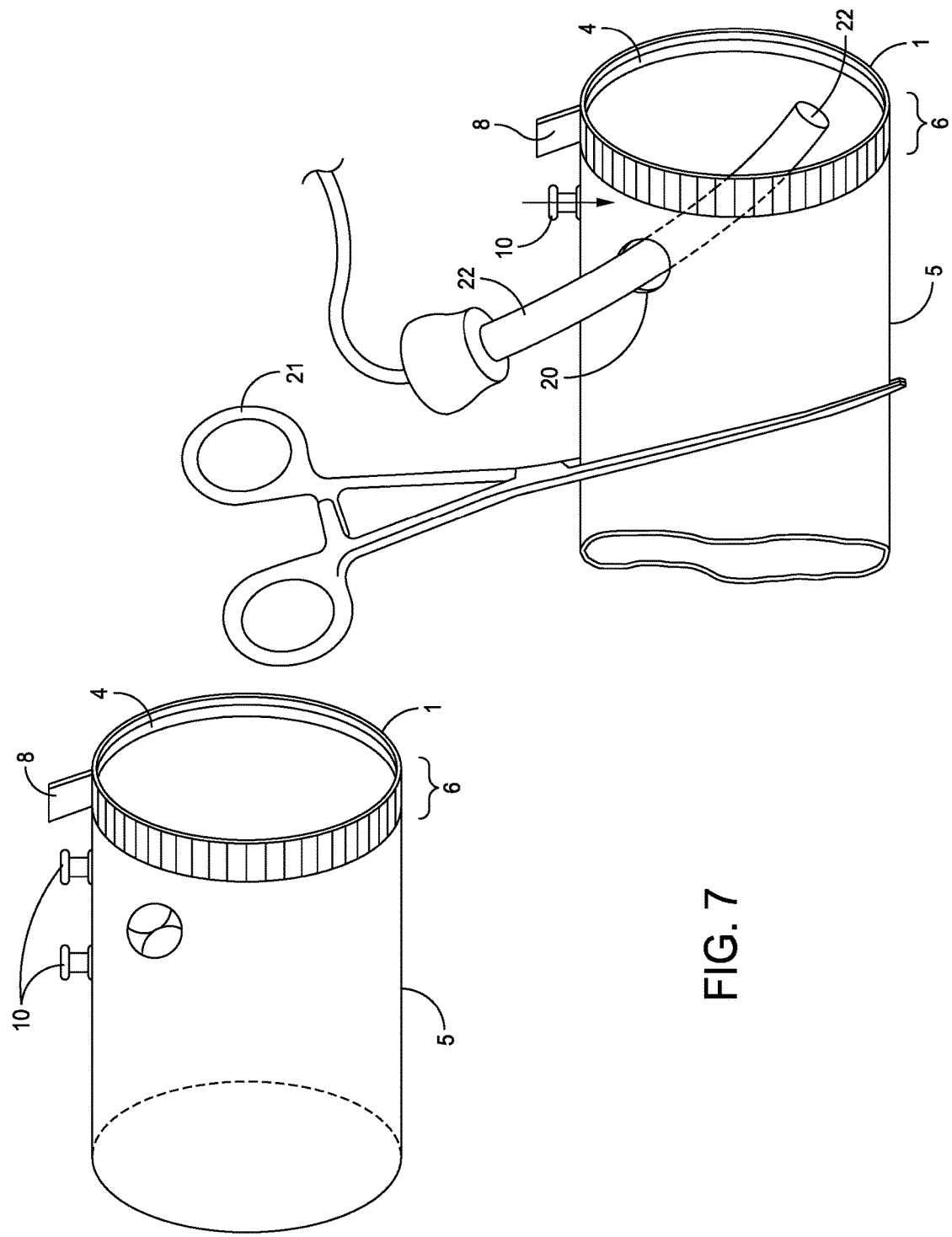
FIG. 7 is a representation of a device comprising a tube containing a port or one-way valve for receiving of a video-scope or ultrasound probe.

Embodiments are envisioned wherein the device comprises a tube/cylinder comprised of fabric or other material that is sutured to the opened or transected aorta or ventriculo-aortic junction, and the aortic valve is accessed by making incisions in the tube/cylinder close to the point of attachment, and re-approximating those incisions in order to make valve re-assessments (to re-create a water-tight seal). One iteration of such device is illustrated in FIG. 7. The proximal end 6 of the device is sutured to the opened or transected aorta, or to the ventriculo-aortic junction (during aortic root replacement with aortic valve re-implantation). The distal end of tube/cylinder 5 may be closed, or open, but able to be clamped with a standard aortic vascular clamp 21, while filling the tube or cylinder 5 with fluid by needle puncture, Luer lock connector or other port 10. Other ports 10 may be used to monitor pressure or as relief valves. Port site 20 may comprise a one-way valve for insertion of a video-scope or ultrasound transducer 22. In such a fashion, the valve may be indirectly visualized during simulated diastolic conditions by a video camera, for example. In some iterations, a transparent window is incorporated into the tube (not shown) to allow for direct visualization of the valve. The clamp 21 is removed and the valve can be repaired or re-repaired either through the open distal end of tube or cylinder 5, or by making an incision in the fabric of the tube near the proximal end 6. Such an incision could be re-sutured after valve repair is performed, so that a water-tight seal again may be achieved. Again, the tube/cylinder 5 is clamped 21 and diastolic conditions simulated by fluid filling the tube, possibly by a port 10, and the repair evaluated by a video-scope 22, for example, placed through port or one-way valve 20. The process is repeated until a satisfactory result is obtained, and then the device is transected just beyond the proximal end 6, which can be further sewn to the distal transected aorta to complete surgery.

FIGS. 8A-8F show another embodiment of the device comprising a tube/cylinder 5 made of fabric (e.g., polyester) or other synthetic material. The tube/cylinder 5 is attached non-reversibly at its proximal end 6 to the aorta or to the ventriculo-aortic junction (as in aortic root replacement with aortic valve re-implantation. A feature of the tube/cylinder 5 is that it can be collapsed down to a much shorter length (i.e., less than 50% of its original length) in order to facilitate visualization and manipulation of the valve without the encumbrance of a bulky device. Tube or cylinder 5 (FIG. 8A) may be configured to roll down externally to achieve a partially roll down configuration 23 (FIG. 8B) or a fully collapsed 24 configuration (FIG. 8C). Another iteration of the device shows an accordion-type design (FIG. 8D) with corrugations that collapse down to a minimum and are held in place by temporary sutures 25 (FIG. 8E). The tube or cylinder 5 may comprise one or more Luer lock connectors 10 or other ports 20, possibly comprising a one-way valve. In the unfurled or extended position, the distal end of tube or cylinder 5 can be clamped with an aortic vascular clamp (as in FIG. 7, clamp 21, not shown in this figure) and diastole simulated. The valve can then be assessed either indirectly, by a video-scope or ultrasound placed via port 20, or directly if tube/cylinder 5 is transparent or comprises a transparent window, as opposed to being made (partially or completely) from fabric. The clamp is removed, and the tube or cylinder 5 collapses down to a short length 24, ideally less than 50% of its extended length (FIG. 8F). The valve leaflets L are visualized and manipulated and the process repeated until satisfactory. Not shown but intended is the possibility of incorporating a cinch mechanism into proximal end 6.

Figure 9C:
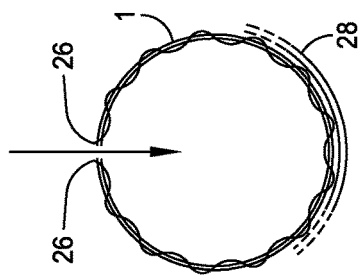
FIGS. 9A-9E illustrate views of a cinching or snaring mechanism incorporated into a short open tube with at least one integrated purse-string suture.
Figure 9E:
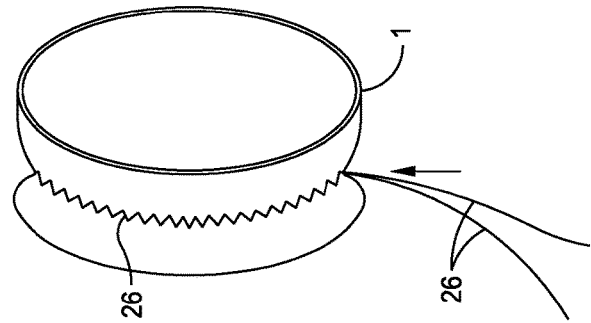
Figure 9B:
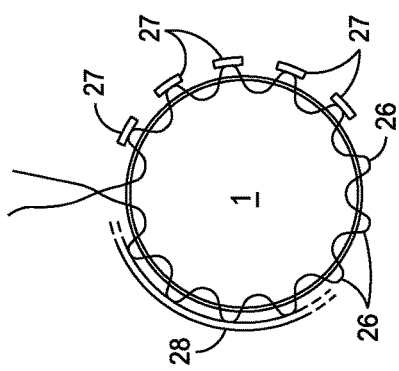
Figure 9A:
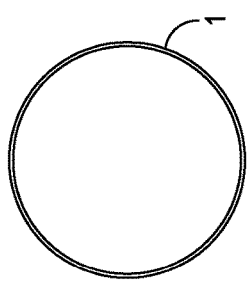
Figure 9D:
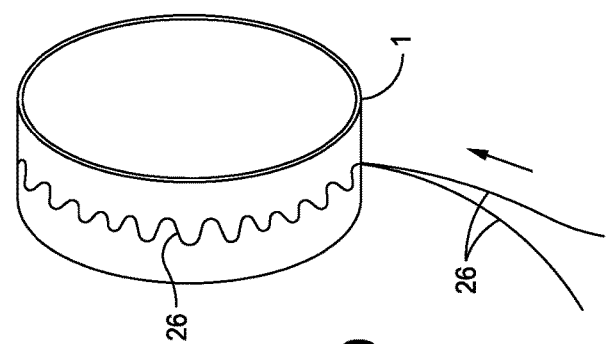

FIGS. 9A-9E show a general cinch mechanism that may be incorporated into the proximal end 6 of the short open tube 1, shown axially in FIGS. 9A-9C. At least one suture 26 is woven in and out of the circumference of the short open tube in a purse-string fashion. Polytetrafluoroethylene (PTFE) or other material pledgets 27 or a continuous strip of fabric or material 28 may be integrated or fused to the short open tube 1 and used to diminish bleeding points due to the passed suture 26. In FIG. 9C, the short open tube 1 is discontinuous (at arrow) yet still has integrated purse-string or strings 26. Multiple purse-string sutures may be incorporated in order to asymmetrically narrow the purse-string if desired (not shown). When the purse-string suture is cinched or tied, the short open tube 1 is transformed into a structure of smaller diameter 28 (FIG. 9E), which may be a useful adjunct in aortic valve repair. A view from the side shows a typical pinched in appearance to short open tube 1 along suture line 26.

Figure 10B:
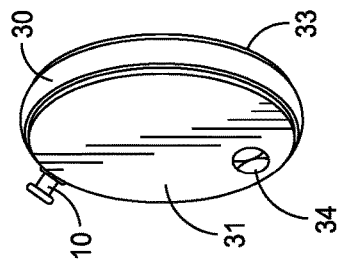
FIGS. 10A-10C illustrate another embodiment of a disc or distally closed cylinder having an axially arranged groove to enable reversible attachment by an external cinch or snare associated with a short open tube or the aorta itself.
Figure 10C:
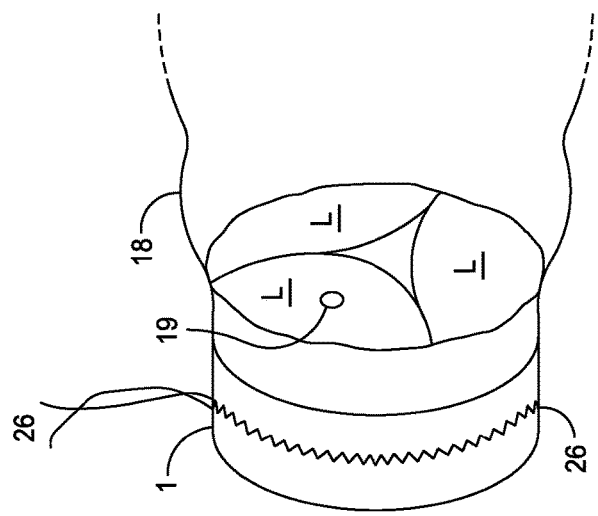
Figure 10A:
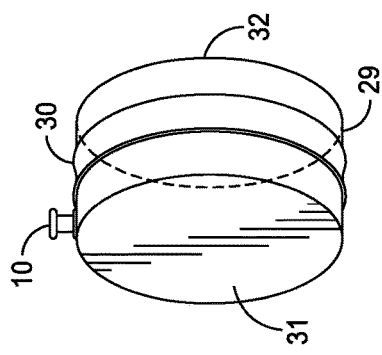

FIGS. 10A-10C illustrate a short cylinder 29 (transparent and closed on its distal end 31, and open on its proximal end 32) or a transparent disc 33, each comprising a reversible connecting mechanism 30 with the short open tube 1 by the connecting mechanism 35 associated with the aortic root 18. The connecting mechanism 30 may comprise a groove or ridge, and when short cylinder 29 or disc 33 are placed within the short open tube 1, a cinching mechanism 26 may be used to snare into the ridge or groove to reversibly fix the cylinder 29 or disc 33 within the short open tube 1. Alternatively, the connecting mechanism 30 and the cinching mechanism 26 may instead comprise a magnet and a ferromagnetic core to allow for reversible coupling, as previously described. Diastole is simulated by the Luer lock connector or other port 10, and pressure regulation or overflow valve control may be incorporated 34. The valve is inspected through the transparent surface 31 and then the cylinder 29 or disc 33 is separated from the short open tube 1, which has been attached to the aortic root 18 either at the level of the transected aorta above the valve, or at the ventriculo-aortic junction (as in aortic root replacement with aortic valve re-implantation). Valve repair or re-repair is performed and the process repeated until a satisfactory result is obtained. The short open tube 1 is then sewn to the distal transected aorta to complete surgery.

FIG. 11 shows an embodiment of a transparent disc 33 that reversibly couples directly to a transected or opened aorta. A generally circumferential groove or ridge 30 is snared within the aorta 18 that has been opened distal to the valve leaflets L. Reversible coupling of the disc 33 to the aorta 18 is accomplished by external snaring 35. The diastolic state of the aortic root 18 is simulated by infusion of clear fluid via port 10, provided by tubing 16. Surface 31 is partially or completely transparent, or may comprise a magnification or distortion lens.

Figure 12:
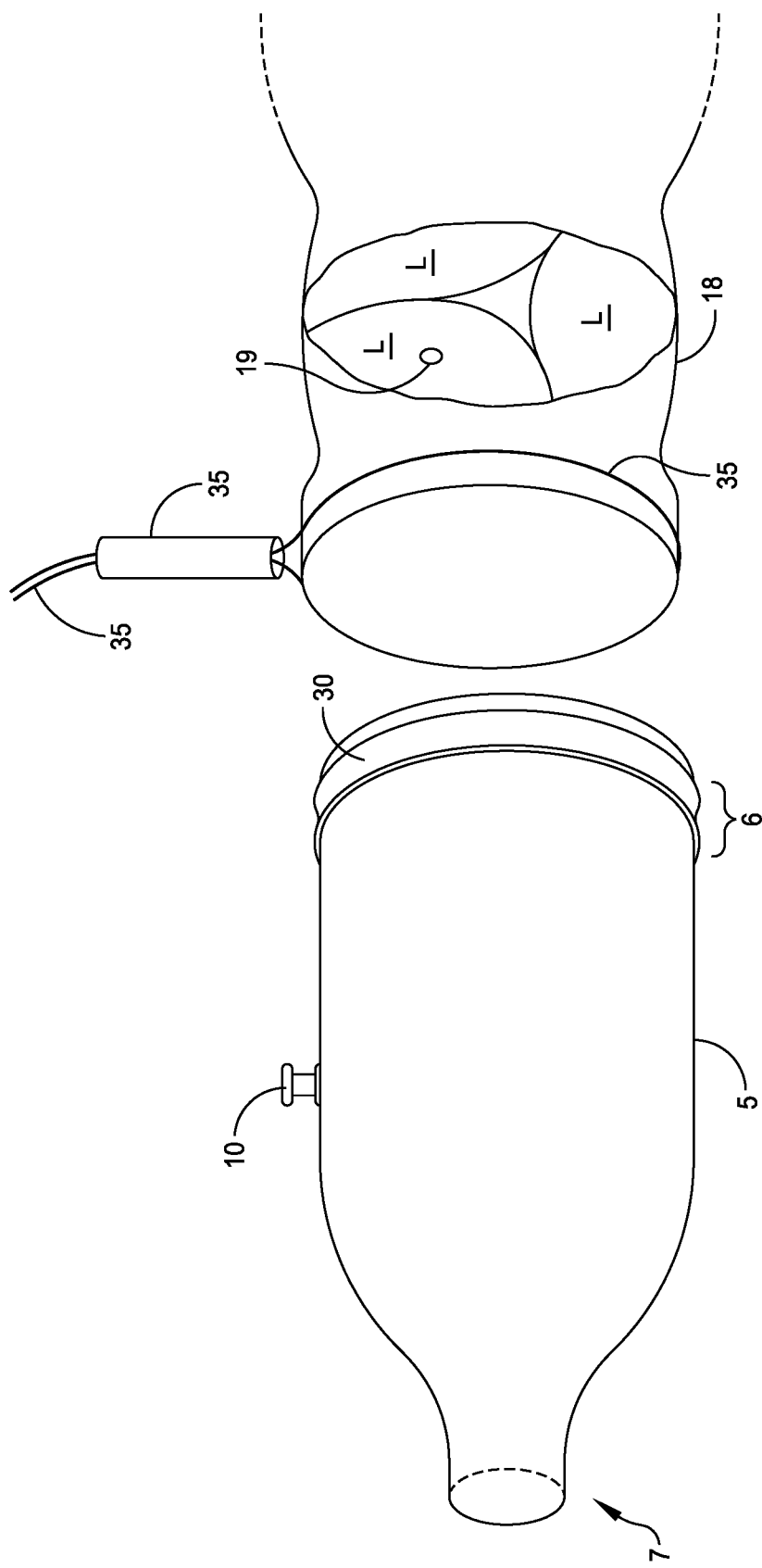
FIG. 12 illustrates a representation of the device as a transparent chamber, which has a groove or ridge peripherally oriented on its proximal open end that can be snared externally within the aorta or a short tube.

FIG. 12 shows another embodiment of the mechanism for reversible coupling of transparent cylinder 5. In this iteration, proximal open end 6 comprises a generally circumferential ridge or groove 30 that can be reversibly attached to the aorta 18 or a short open tube (not shown) via an external snare 35. Groove or ridge 30 is placed inside of aorta 18 and external snare 35 is outside of aorta 18 (or short open tube, not shown), and keeps the entire chamber 5 firmly in place, and in a generally water-tight configuration. Fluid for pressurization of the aortic root is infused via distal end 7, and pressure can be monitored via port 10.

Embodiments of the present disclosure are directed to a vascular prosthetic graft that is adjustable in a dynamic fashion both in terms of longitudinal cylinder length as well as diameter/caliber. Such a graft is configured to avoid situations of excessive graft length or tension on grafts that become too short, and also facilitate more hydrostatic and hemostatic vascular connections by the ability to adjust and match diameter near the level of vascular/graft connections.

Embodiments of the present disclosure include a prosthetic graft device that is available in a variety of calibers and total lengths to match specific procedural needs and native blood vessel dimensions. Generally speaking, the prosthetic vascular graft device is constructed of a material that does not appreciably expand either radially or axially simply with increasing physiologic hydrostatic (blood) luminal pressures compared with baseline uncompressed dimensions. In one embodiment, the graft device embodies a very short cylinder whose adjustable and expandable length is present in the form of an external rolled down graft segment or segments (at either end), that can be rolled out or rolled back down in order to adjust to an ideal length after completing the first of two vascular connections. With such a device, the connection of the native blood vessel can be performed to a very short graft, which enhances visibility and ease (and hydro/hemostatic nature) of the hand-sewn vascular connection. When the graft is short in length, passage of sutures can be done from either inside or outside of the graft, which is a significant technical advantage for the operator.

In one embodiment, the prosthetic graft has rolled down components at both ends, with a short intervening segment of graft in between the two ends. To create a vascular bypass or connection of truly ideal length, three vascular/graft connections may be made in the following fashion. A single prosthetic graft is transected across a short intact intervening segment, leaving behind two roll-down grafts, each with a short attached cylindrical (non-rolled) graft segment (previously the short intervening segment). Vascular connections are made to each target recipient vessel in the standard fashion, and then, the rolled down components are un-rolled towards one another to achieve the perfect length, and residual rolled up segments are simply connected to one another with standard suture techniques. The latter roll-to-roll segment vascular connection is expected to be more hemostatic than a typical graft-to-graft connection with sutures because the residual bulk of the rolled up graft areas includes substantially greater surface area to prevent bleeding at the areas of connection.

Other embodiments of the graft device include a specific mechanism to promote the rolled down segments having device "memory" in order to maintain or create the rolled down shape when desired. One mechanism may include integrated shape memory alloys (e.g., nitinol) along the body of the graft in one or more "spines." Other mechanisms may be employed to perform the method of extrusion of the prosthetic graft. Certain embodiments of these graft devices may include side branches that may also include roll-down graft segments in order to facilitate secondary branch graft connections, similar to non-rolled branch graft devices currently in use, but taking advantage of the adjustability and hemostatic nature of the aforementioned embodiments.

Another aspect of the disclosure relates to the ability to adjust the caliber or diameter of the graft in at least one or more areas of the graft, in order to facilitate caliber-matching or adjustability of the connection to intended targets. In one embodiment, this is accomplished with integrated total or partial circumferential purse-string sutures that can be cinched or tied in real-time in order to down-size the caliber of that segment of the prosthetic graft. In another embodiment, these caliber or diameter adjustments can be accomplished by manipulation of similarly integrated shape memory alloy or polymer. In yet another embodiment, miniature externally actuated ratchet systems can be integrated in locations around the prosthetic graft circumference to create reversible/adjustable diameter reduction as desired.

Figure 13A:
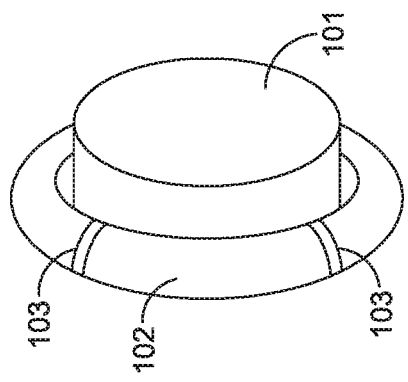
FIGS. 13A-13C illustrate a cylinder-shaped vascular graft device that rolls down to a minimal length while maintaining the same internal diameter, and has memory to stay rolled down by virtue of a shape memory mechanism integral to the graft.

FIG. 13A shows a prosthetic vascular graft including a body fabricated from generally flexible material that is cylindrical in shape. As shown, there is a straight, unrolled portion of the body of the graft 101 and a rolled down portion 102 of the graft 101 that is maintained in a rolled down configuration by virtue of a shape memory mechanism. In the shown example, the body of the graft 101 is maintained by one or more strips of a shape memory alloy 103, e.g., three strips of shape memory alloy, which are also rolled down with the rolled down portion or segment 102 of the graft 101 in this illustration. The mechanism 103 can be triggered by applying heat, for example.

Figure 13B:
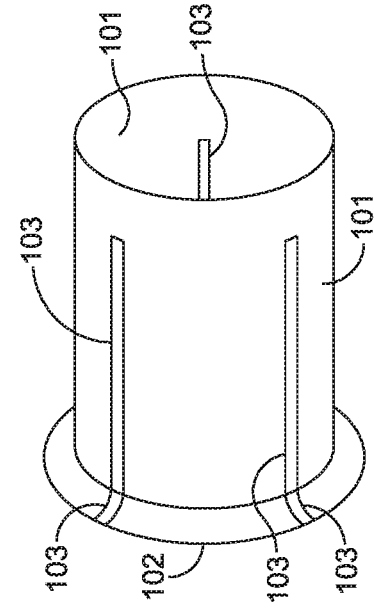

FIG. 13B illustrates the body of the prosthetic vascular graft 101 having been rolled out to extend its length. The rolled down portion 102 of the graft 101 is smaller in bulk, since portions of the graft become part of the un-rolled segment of graft. A mechanism embodying the strips of shape memory alloy 103 of the graft 101 maintains the graft in the rolled down or baseline configuration. In one embodiment, the mechanism 103 embodies strips of shape memory alloy, e.g., nitinol, which are integrated into the wall of the graft 101, and cause the flexible graft material to roll backwards to a point where the shape memory strips terminate, as shown in FIG. 1A. In the shown embodiment, the mechanism 103 embodies three strips of shape memory material to extend the body of the cylinder. However, any number of strips can be provided.

Figure 13C:
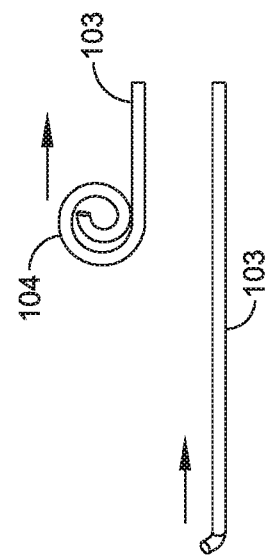

FIG. 13C shows an example of how the strips of shape memory material 103 (or polymer) appear to be rolled backwards on itself at 104 in its baseline configuration, and can be rolled out to be straight. When not physically doing something to keep the strip 103 lengthened, the shape memory causes it to revert to a rolled down state 104.

FIG. 14A shows an embodiment of the device wherein there is a rolled down component 102 on each opposing end of a non-rolled segment of graft 101. The strips of shape memory material 103 cause the graft 101 to roll down and backwards onto itself, similar to the operation of a condom.

This embodiment also shows examples of an integrated purse-string 105 or a belt 110 and loops 109 system for narrowing the caliber of the cylindrical tube graft 101.

FIG. 14B shows another embodiment of the cylindrical prosthetic graft 101 comprising a roll-down component 102, and its roll-down mechanism shape memory strips 103, as well as cylindrical side branches 106 that also include their own roll-down segments 107 and roll-down mechanisms 108, again shown here as integrated strips of shape memory alloy or polymer 108.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:

1. A prosthetic device for attachment to a vascular structure, the device comprising:
   (a) a flexible tube;
   (b) a lumen defined within the flexible tube, wherein the lumen extends from a first opening at a first end to a second opening at a second end;
   (c) an attachment structure at the first end;
   (d) a roll-down segment disposed at the second end, wherein the roll-down segment comprises at least:
      (i) a fully extended configuration, wherein the flexible tube is at full length; and
      (ii) a fully collapsed configuration, wherein the flexible tube is at less than 50% of full length; and
   (d) a roll-down mechanism operably coupled with the roll-down segment, wherein the roll-down mechanism is configured to urge the roll-down segment between the fully extended configuration and the fully collapsed configuration.

2. The prosthetic device of claim 1, wherein the roll-down segment further comprises a partially extended configuration, wherein the roll-down segment is disposed at a position between the fully extended configuration and the fully collapsed configuration.

3. The prosthetic device of claim 1, wherein the roll-down segment is moveable between the fully extended configuration and the fully collapsed configuration.

4. The prosthetic device of claim 1, wherein the roll-down mechanism comprises a shape memory structure, wherein the shape memory structure is biased toward the fully collapsed configuration.

5. The prosthetic device of claim 1, wherein the fully collapsed configuration comprises a Swiss roll-like shape.

6. The prosthetic device of claim 1, further comprising a diameter adjustment structure disposed along a length of the flexible tube.

7. The prosthetic device of claim 6, wherein the diameter adjustment structure comprises a purse-string suture or a shape memory diameter adjustment structure.

8. The prosthetic device of claim 1, further comprising at least one cylindrical side branch extending from the flexible tube, the at least one cylindrical side branch comprising:
   (a) a flexible side tube;
   (b) a side tube lumen defined within the flexible side tube, wherein the side tube lumen extends from a first side tube opening at a first side tube end to a second side tube opening at a second side tube end, wherein the first side tube opening is in fluidic communication with the lumen of the flexible tube; and
   (c) a side tube roll-down segment disposed at the second side tube end.

9. The prosthetic device of claim 1, wherein the attachment structure is a suturable material, wherein the suturable material is suturable to the vascular structure.

10. A prosthetic device for attachment to a vascular structure, the device comprising:
    (a) a flexible tube;
    (b) a lumen defined within the flexible tube, wherein the lumen extends from a first opening at a first end to a second opening at a second end;
    (c) a first roll-down segment disposed at the first end, wherein the first roll-down segment comprises at least:
       (i) a first fully extended configuration; and
       (ii) a first fully collapsed configuration;
    (d) a first roll-down mechanism operably coupled with the first roll-down segment, wherein the first roll-down mechanism is configured to urge the first roll-down segment between the first fully extended configuration and the first fully collapsed configuration;
    (e) a second roll-down segment disposed at the second end, wherein the roll-down segment comprises at least:
       (i) a second fully extended configuration; and
       (ii) a second fully collapsed configuration; and
    (f) a second roll-down mechanism operably coupled with the second roll-down segment, wherein the second roll-down mechanism is configured to urge the second roll-down segment between the second fully extended configuration and the second fully collapsed configuration.

11. The prosthetic device of claim 10, wherein the first fully extended configuration comprises the first end at full length and the second fully extended configuration comprises the second end at full length.

12. The prosthetic device of claim 10, wherein
    the first roll-down segment further comprises a first partially extended configuration, wherein the first roll-down segment is disposed at a position between the first fully extended configuration and the first fully collapsed configuration, and
    the second roll-down segment further comprises a second partially extended configuration, wherein the second roll-down segment is disposed at a position between the second fully extended configuration and the second fully collapsed configuration.

13. The prosthetic device of claim 10, wherein the first roll-down segment is moveable between the first fully extended configuration and the first fully collapsed configuration, and wherein the second roll-down segment is moveable between the second fully extended configuration and the second fully collapsed configuration.

14. The prosthetic device of claim 10, wherein
    the first roll-down mechanism comprises a first shape memory structure, wherein the first shape memory structure is biased toward the first fully collapsed configuration, and
    the second roll-down mechanism comprises a second shape memory structure, wherein the second shape memory structure is biased toward the second fully collapsed configuration.

15. The prosthetic device of claim 10, further comprising a diameter adjustment structure disposed along a length of the flexible tube, wherein the diameter adjustment structure comprises a purse-string suture or a shape memory diameter adjustment structure.

16. A method of attaching a prosthetic device to a vascular structure, the method comprising:

attaching a first end of a flexible tube to the vascular structure, the flexible tube comprising:
  (a) a lumen defined within the flexible tube;
  (b) a roll-down segment disposed at a second end of the flexible tube, wherein the roll-down segment comprises at least:
    (i) a fully extended configuration, wherein the flexible tube is at full length; and
    (ii) a fully collapsed configuration, wherein the flexible tube is at less than 50% of full length; and
  (c) a roll-down mechanism operably coupled with the roll-down segment, wherein the roll-down mechanism is configured to urge the roll-down segment between the fully extended configuration and the fully collapsed configuration; and
extending the roll-down segment toward a fully extended configuration.

17. The method of claim 16, further comprising closing off the second end of the flexible tube after extending the roll-down segment toward the fully extended configuration.

18. The method of claim 17, wherein the closing off the second end comprises using a clamp to close off the second end.

19. The method of claim 16, further comprising attaching the second end of the flexible tube to a second vascular structure after extending the roll-down segment toward the fully extended configuration.

20. The method of claim 19, further comprising adjusting a diameter of the flexible tube to substantially match a diameter of the vascular structure.

* * * * *